United States Patent [19]
Duvick et al.

[11] Patent Number: 5,716,820
[45] Date of Patent: Feb. 10, 1998

[54] FUMONISIN DETOXIFICATION ENZYMES

[75] Inventors: Jon Duvick; Tracy Rood, both of Des Moines; Xun Wang, Ames, all of Iowa

[73] Assignee: Pioneer Hi-Bred International, Inc., Des Moines, Iowa

[21] Appl. No.: 805,814

[22] Filed: Feb. 26, 1997

Related U.S. Application Data

[62] Division of Ser. No. 289,595, Aug. 12, 1994, abandoned.

[51] Int. Cl.$^6$ .............................. C12N 9/16; C12N 9/14
[52] U.S. Cl. ...................... 435/196; 435/195; 435/197
[58] Field of Search ............................ 435/195, 196, 435/197

[56] References Cited

U.S. PATENT DOCUMENTS

| | | | |
|---|---|---|---|
| 4,988,586 | 1/1991 | Toyoda et al. | 424/93.2 |
| 5,178,863 | 1/1993 | Toyoda et al. | 424/93.48 |
| 5,262,306 | 11/1993 | Robeson et al. | 435/29 |

OTHER PUBLICATIONS

Abbas, et al. (1992) Phytotoxicity of Fumonisin $B_1$ on Weed and Crop Species[1], *Weed Technology*, vol. 6:548–552.

Blackwell, et al. (1994) Production of Carbon 14–Labeled Fumonisin in Liquid Culture, *Journal of AOAC International*, vol. 77, No. 2, pp. 506–511.

Gelderblom, et al. (1993) Structure–Activity Relationships of Fumonisins in Short–Term Carcinogenesis and Cytotoxicity Assays, *Food Chem. Toxic.*, vol. 31, No. 6, pp. 407–414.

Van Asch, et al. (1992) Phytotoxicity of Fumoninsin $B_1$, Moniliformin, and T–2 Toxin to Corn Callus Cultures, *Phytopathology*, vol. 82, No. 11, pp. 1330–1332.

Vesonder, et al. (1993) Comparison of the Cytotoxicities of Fusarium Metabolites and Alternaria Metabolite AAL–Toxin to Cultured Mammalian Cell Lines, *Arch. Environ. Contam. Toxicol.*, vol. 24, pp. 473–477.

Tanaka, et al. (1993) Structure–Dependent Phytotoxicity of Fumonisins and Related Compounds in a Duckweed Bioassay, *Phytochemistry*, vol. 33, No. 4, pp. 779–785.

He P., et al. (1992) Microbial Transformation of Deoxynivalenol (Vomitoxin), *Applied and Environmental Microbiology*, vol. 58, No. 12, pp. 3857–3863.

Kneusel, et al. (1994) Molecular Characterization and Cloning of an Esterase Which Inactivates the Macrolide Toxin Brefeldin A*, *The Journal of Biological Chemistry*, vol. 269, No. 5, pp. 3449–3456.

Miller, J. D., et al. (1986) Degradation of deoxynivalenol by suspension cultures of the fusarium head blight resistant wheat cultivar Frontana, *Canadian Journal of Plant Pathology*, vol. 8, pp. 147–150.

Ueno, et al. (1983) Metabolism of T–2 Toxin in Curtobacterium sp. Strain 114–2, *Applied and Environmental Microbiology*, vol. 46, pp. 120–127.

Utsumi, et al. (1991) Molecular Cloning and Characterization of the Fusaric Acid–resistance Gene from *Pseudomonas cepacia*, *Agric. Biol. Chem.*, vol. 55, pp. 1913–1918.

Vesonder, et al. (1992) Comparative Phytotoxicity of the Fumonisins, AAL–Toxin and Yeast Sphingolipids in *Lemna minor* L. (Duckweed), *Arch. Environ. Contam. Toxicol.*, vol. 23, pp. 464–467.

Marth, et al. (1978) Update on molds: degradation of aflatoxin, *J. Food Technol.*, 33:81–87.

Kneusel, et al. (1990) Detoxification of the macrolide toxin brefeldin A by *Bacillus subtillis*, *FEBS Letters*, vol. 275, No. 1,2, pp. 107–110.

Toyoda, et al. (1988) Detoxification of Fusaric Acid by a Fusaric Acid–Resistant Mutant of *Pseudomonas solanacearum* and its Applicaation to Biolgoical Control of Fusarium Wilt of Tomato, *Phytopathology*, vol. 78, No. 10, p. 1307–1311.

Bunz et al. (1993) Purification of two isosfunctional hydrolases (EC 2.7.1.8) in the degradative pathway for dibenzofuran in Sphingomonas sp. strain RW1, *Biodegradation*, 4:171–178.

Duvick et al. (1992) Purification and Characterization of a Novel Antimicrobial Peptide from Maize (*Zea mays* L.) Kernels*, *The Journal of Biological Chemistry*, vol. 267, No. 26, pp. 18814–18820.

*Primary Examiner*—Keith D. Hendricks

[57] ABSTRACT

Methods for identifying organisms capable of degrading fumonisin. Fumonisin can be incorporated into culture medium for selection of organisms resistant to fumonisin. Using this method, several organisms have been identified. These organisms can be used to isolate the enzyme and the gene responsible for conferring fumonisin-resistance. The gene can be cloned and inserted into a suitable expression vector so that the protein can be further characterized. Additionally, the DNA encoding for fumonisin-resistance can be used to transform plant cells normally susceptible to Fusarium infection. Plants can be regenerated from the transformed plant cells. In this way, a transgenic plant can be produced with the capability of degrading fumonisin.

3 Claims, No Drawings

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 32 bases
        ( B ) TYPE: nucleotide
        ( C ) STRANDEDNESS: single
        ( D ) TOPOLOGY: linear ( i i ) MOLECULE TYPE: probe ( i i i ) HYPOTHETICAL: NO ( i v ) ANTI-SENSE: NO ( x i ) SEQUENCE DESCRIPTION: SEQ ID NO:1:

GGGGAATTCG ARGAYTGNYT NTAYNTNAAY RT        32

( 2 ) INFORMATION FOR SEQ ID NO:2:

( i ) SEQUENCE CHARACTERISTICS:
        ( A ) LENGTH: 37 bases
        ( B ) TYPE: nucleotide
        ( C ) STRANDEDNESS: single
        ( D ) TOPOLOGY: linear ( i i ) MOLECULE TYPE: probe ( i i i ) HYPOTHETICAL: NO ( i v ) ANTI-SENSE: NO ( x i ) SEQUENCE DESCRIPTION: SEQ ID NO:2:

GGGGAATTCM CNGTNNTNVT NTGGATNYAY GGNGGNG        37

( 2 ) INFORMATION FOR SEQ ID NO:3:

( i ) SEQUENCE CHARACTERISTICS:
        ( A ) LENGTH: 35 bases
        ( B ) TYPE: nucleotide
        ( C ) STRANDEDNESS: single
        ( D ) TOPOLOGY: linear ( i i ) MOLECULE TYPE: probe ( i i i ) HYPOTHETICAL: NO ( i v ) ANTI-SENSE: NO ( x i ) SEQUENCE DESCRIPTION: SEQ ID NO:3:

GGGAAGCTTG GRTYNCCNCC RAANKBNGCD ATRTT        35

( 2 ) INFORMATION FOR SEQ ID NO:4:

( i ) SEQUENCE CHARACTERISTICS:
        ( A ) LENGTH: 36 bases
        ( B ) TYPE: nucleotide
        ( C ) STRANDEDNESS: single
        ( D ) TOPOLOGY: linear ( i i ) MOLECULE TYPE: probe ( i i i ) HYPOTHETICAL: NO ( i v ) ANTI-SENSE: NO ( x i ) SEQUENCE DESCRIPTION: SEQ ID NO:4:

GGGAAGCTTC NCCNGCNSWY TCNCCRAANA DNGTNA    36

( 2 ) INFORMATION FOR SEQ ID NO:5:

( i ) SEQUENCE CHARACTERISTICS:
        ( A ) LENGTH: 76 amino acid
        ( B ) TYPE: amino acid
        ( C ) STRANDEDNESS: single
        ( D ) TOPOLOGY: linear ( i i ) MOLECULE TYPE: protein (partial)

( i i i ) HYPOTHETICAL: NO ( i v ) ANTI-SENSE: NO ( x i ) SEQUENCE DESCRIPTION: SEQ ID NO:5:

```
Ser Phe His Leu Tyr Asp Gly Ala Ser Phe Ala Ala Asn Gln Asp
                  5                  10                 15
Val Ile Val Val Thr Ile Asn Tyr Arg Thr Asn Ile Leu Gly Phe
                 20                  25                 30
Pro Ala Ala Pro Gln Leu Pro Ile Thr Gln Arg Asn Leu Gly Phe
                 35                  40                 45
Leu Asp Gln Arg Phe Ala Leu Asp Trp Val Gln Arg Asn Ile Ala
                 50                  55                 60
Ala Phe Gly Gly Asp Pro Arg Lys Val Thr Phe Phe Gly Glu Ser
                 65                  70                 75
Ala
```

( 2 ) INFORMATION FOR SEQ ID NO:6:

( i ) SEQUENCE CHARACTERISTICS:
        ( A ) LENGTH: 23 bases
        ( B ) TYPE: nucleotide
        ( C ) STRANDEDNESS: single
        ( D ) TOPOLOGY: linear ( i i ) MOLECULE TYPE: probe ( i i i ) HYPOTHETICAL: NO ( i v ) ANTI-SENSE: NO ( x i ) SEQUENCE DESCRIPTION: SEQ ID NO:6:

GCTAGTTTCG CAGCCAATCA GGA    23

( 2 ) INFORMATION FOR SEQ ID NO:7:

( i ) SEQUENCE CHARACTERISTICS:
        ( A ) LENGTH: 23 bases
        ( B ) TYPE: nucleotide
        ( C ) STRANDEDNESS: single
        ( D ) TOPOLOGY: linear ( i i ) MOLECULE TYPE: probe ( i i i ) HYPOTHETICAL: NO ( i v ) ANTI-SENSE: NO ( x i ) SEQUENCE DESCRIPTION: SEQ ID NO:7:

AAAGGCTGCG ATGTTCCGCT GTA    23

( 2 ) INFORMATION FOR SEQ ID NO:8:

( i ) SEQUENCE CHARACTERISTICS:
        ( A ) LENGTH: 23 bases (B) TYPE: nucleotide
(C) STRANDEDNESS: single
(D) TOPOLOGY: linear (ii) MOLECULE TYPE: probe (iii) HYPOTHETICAL: NO (iv) ANTI-SENSE: NO (xi) SEQUENCE DESCRIPTION: SEQ ID NO:8:

TCGCTGTGTT ATTGGCAGCT GAG     23

(2) INFORMATION FOR SEQ ID NO:9:

(i) SEQUENCE CHARACTERISTICS:
    (A) LENGTH: 28 bases
    (B) TYPE: nucleotide
    (C) STRANDEDNESS: single
    (D) TOPOLOGY: linear (ii) MOLECULE TYPE: probe (iii) HYPOTHETICAL: NO (iv) ANTI-SENSE: NO (xi) SEQUENCE DESCRIPTION: SEQ ID NO:9:

CGCGGATCCG TTTTTTTTT TTTTTTV     28

(2) INFORMATION FOR SEQ ID NO:10:

(i) SEQUENCE CHARACTERISTICS:
    (A) LENGTH: 527 amino acids
    (B) TYPE: amino acid
    (C) STRANDEDNESS: single
    (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:10:

| Met | Pro | Ser | Arg | Tyr | Ile | Leu | Ser | Trp | Leu | Leu | Thr | Cys | Phe | Leu |
|---|---|---|---|---|---|---|---|---|---|---|---|---|---|---|
|   |   |   |   | 5 |   |   |   |   | 10 |   |   |   |   | 15 |
| Gly | Ile | Ala | Phe | Gly | Ser | Arg | Cys | Gly | Ser | Ser | Ala | Pro | Thr | Val |
|   |   |   |   | 20 |   |   |   |   | 25 |   |   |   |   | 30 |
| Lys | Ile | Asp | Ala | Gly | Met | Val | Val | Gly | Thr | Thr | Thr | Thr | Val | Pro |
|   |   |   |   | 35 |   |   |   |   | 40 |   |   |   |   | 45 |
| Gly | Thr | Thr | Ala | Thr | Val | Ser | Glu | Phe | Leu | Gly | Val | Pro | Phe | Ala |
|   |   |   |   | 50 |   |   |   |   | 55 |   |   |   |   | 60 |
| Ala | Ser | Pro | Thr | Arg | Phe | Ala | Pro | Pro | Thr | Arg | Pro | Val | Pro | Trp |
|   |   |   |   | 65 |   |   |   |   | 70 |   |   |   |   | 75 |
| Ser | Thr | Pro | Leu | Gln | Ala | Thr | Ala | Tyr | Gly | Pro | Ala | Cys | Pro | Gln |
|   |   |   |   | 80 |   |   |   |   | 85 |   |   |   |   | 90 |
| Gln | Phe | Asn | Tyr | Pro | Glu | Glu | Leu | Arg | Glu | Ile | Thr | Met | Ala | Trp |
|   |   |   |   | 95 |   |   |   |   | 100 |   |   |   |   | 105 |
| Phe | Asn | Thr | Pro | Pro | Pro | Ser | Ala | Gly | Glu | Ser | Glu | Asp | Cys | Leu |
|   |   |   |   | 110 |   |   |   |   | 115 |   |   |   |   | 120 |
| Asn | Leu | Asn | Ile | Tyr | Val | Pro | Gly | Thr | Glu | Asn | Thr | Asn | Lys | Ala |
|   |   |   |   | 125 |   |   |   |   | 130 |   |   |   |   | 135 |
| Val | Met | Val | Trp | Ile | Tyr | Gly | Gly | Ala | Leu | Glu | Tyr | Gly | Trp | Asn |
|   |   |   |   | 140 |   |   |   |   | 145 |   |   |   |   | 150 |

| | | | | | | | | | | | | | |
|---|---|---|---|---|---|---|---|---|---|---|---|---|---|
| Ser | Phe | His | Leu | Tyr 155 | Asp | Gly | Ala | Ser | Phe 160 | Ala | Ala | Asn | Gln | Asp 165 |
| Val | Ile | Val | Val | Thr 170 | Ile | Asn | Tyr | Arg | Thr 175 | Asn | Ile | Leu | Gly | Phe 180 |
| Pro | Ala | Ala | Pro | Gln 185 | Leu | Pro | Ile | Thr | Gln 190 | Arg | Asn | Leu | Gly | Phe 195 |
| Leu | Asp | Gln | Arg | Phe 200 | Ala | Leu | Asp | Trp | Val 205 | Gln | Arg | Asn | Ile | Ala 210 |
| Ala | Phe | Gly | Gly | Asp 215 | Pro | Arg | Lys | Val | Thr 220 | Ile | Phe | Gly | Gln | Ser 225 |
| Ala | Gly | Gly | Arg | Ser 230 | Val | Asp | Val | Leu | Leu 235 | Thr | Ser | Met | Pro | His 240 |
| Asn | Pro | Pro | Phe | Arg 245 | Ala | Ala | Ile | Met | Glu 250 | Ser | Gly | Val | Ala | Asn 255 |
| Tyr | Asn | Phe | Pro | Lys 260 | Gly | Asp | Leu | Ser | Glu 265 | Pro | Trp | Asn | Thr | Thr 270 |
| Val | Gln | Ala | Leu | Asn 275 | Cys | Thr | Thr | Ser | Ile 280 | Asp | Ile | Leu | Ser | Cys 285 |
| Met | Arg | Arg | Val | Asp 290 | Leu | Ala | Thr | Leu | Met 295 | Asn | Thr | Ile | Glu | Gln 300 |
| Leu | Gly | Leu | Gly | Phe 305 | Glu | Tyr | Thr | Leu | Asp 310 | Asn | Val | Thr | Val | Val 315 |
| Tyr | Arg | Ser | Glu | Thr 320 | Ala | Arg | Thr | Thr | Gly 325 | Asp | Ile | Ala | Arg | Val 330 |
| Pro | Val | Leu | Val | Gly 335 | Thr | Val | Ala | Asn | Asp 340 | Gly | Leu | Leu | Phe | Val 345 |
| Leu | Gly | Glu | Asn | Asp 350 | Thr | Gln | Ala | Tyr | Leu 355 | Glu | Glu | Ala | Ile | Pro 360 |
| Asn | Gln | Pro | Asp | Leu 365 | Tyr | Gln | Thr | Leu | Leu 370 | Gly | Ala | Tyr | Pro | Ile 375 |
| Gly | Ser | Pro | Gly | Ile 380 | Gly | Ser | Pro | Gln | Asp 385 | Gln | Ile | Ala | Ala | Ile 390 |
| Glu | Thr | Glu | Val | Arg 395 | Phe | Gln | Cys | Pro | Ser 400 | Ala | Ile | Val | Ala | Gln 405 |
| Asp | Ser | Arg | Asn | Arg 410 | Gly | Ile | Pro | Ser | Trp 415 | Arg | Tyr | Tyr | Tyr | Asn 420 |
| Ala | Thr | Phe | Glu | Asn 425 | Leu | Glu | Leu | Phe | Pro 430 | Gly | Ser | Glu | Val | Tyr 435 |
| His | Ser | Ser | Glu | Val 440 | Gly | Met | Val | Phe | Gly 445 | Thr | Tyr | Pro | Val | Ala 450 |
| Ser | Ala | Thr | Ala | Leu 455 | Glu | Ala | Gln | Thr | Ser 460 | Lys | Tyr | Met | Gln | Gly 465 |
| Ala | Trp | Ala | Ala | Phe 470 | Ala | Lys | Asn | Pro | Met 475 | Asn | Gly | Pro | Gly | Trp 480 |
| Lys | Gln | Val | Pro | Asn 485 | Val | Ala | Ala | Leu | Gly 490 | Ser | Pro | Gly | Lys | Ala 495 |
| Ile | Gln | Val | Asp | Val 500 | Ser | Pro | Ala | Thr | Ile 505 | Asp | Gln | Arg | Cys | Ala 510 |
| Leu | Tyr | Thr | His | Tyr 515 | Tyr | Thr | Glu | Leu | Gly 520 | Thr | Ile | Ala | Pro | Arg 525 |
| Thr | Phe | | | | | | | | | | | | | |

FUMONISIN DETOXIFICATION ENZYMES

CROSS REFERENCE TO PARENT APPLICATION

This is a divisional of the prior application Ser. No. 08/289,595, filed Aug. 12, 1994 now abandoned.

TECHNICAL FIELD

The present invention relates generally to the detection and isolation of fumonisin resistant organisms and to compositions and methods for the in vivo detoxification or degradation of fumonisin. This method has broad application in agricultural biotechnology and crop agriculture and in the improvement of food grain quality.

BACKGROUND OF THE INVENTION

Fungal diseases are common problems in crop agriculture. Many strides have been made against plant diseases as exemplified by the use of hybrid plants, pesticides and improved agricultural practices. However, as any grower or home gardener can attest, the problems of fungal plant disease continue to cause difficulties in plant cultivation. Thus, there is a continuing need for new methods and materials for solving the problems caused by fungal diseases of plants. These problems can be met through a variety of approaches. For example, the infectious organisms can be controlled through the use of agents that are selectively biocidal for the pathogens. Another method is interference with the mechanism by which the pathogen invades the host crop plant. Yet another method, in the case of pathogens that cause crop losses, is interference with the mechanism by which the pathogen causes injury to the host crop plant. Still another method, in the case of pathogens that produce toxins that are undesirable to mammals or other animals that feed on the crop plants, is interference with toxin production, storage, or activity. This invention falls into the latter two categories.

Since their discovery and structural elucidation in 1988. (Bezuidenhout S, Gelderblom W. Gorst-Allman C, Horak R, Marasas W, Spiteller B, Vleggaar R (1988) "Structure elucidation of the fumonisins, mycotoxins from *Fusarium moniliforme*." Journal Chem Soc, Chem Commun 1988: 743–745), fumonisins have been recognized as a potentially serious problem in maize-fed livestock. They are linked to several animal toxicoses including leukoencephalomalacia. (Marasas WFO, Kellerman T S, Gelderblom W C A, Coetzer J A W, Thiel P (1988) "Leukoencephalomalacia in a horse induced by fumonisin B-1 isolated from *Fusarium moniliforme*." Onderstepoort Journal of Veterinary Research 55:197–204; Wilson T M, Ledet A E, Owens D L, Rice L G, Nelson H A (1990) "Experimental liver disease in ponies associated with the ingestion of a corn-based ration naturally contaminated with fumonisin $B_1$," American Association of Veterinary Laboratory Diagnosticians: Abstracts 33rd Annual Meeting, Denver, Colo., Oct. 7–9, 1990., Madison, Wis., USA) and porcine pulmonary edema (Colvin B M, Harrison L R (1992) "Fumonisin-Induced Pulmonary Edema and Hydrothorax in Swine." Mycopathologia 117:79–82). and are also suspected carcinogens (Geary W (1971) Coord Chem Rev 7:81; Gelderblom W C A, Kriek N P J, Marasas W F O, Thiel P G (1991) "Toxicity and Carcinogenicity of the Fusarium-Moniliforme Metabolite, Fumonisin-B 1, in Rats." Carcinogenesis 12:1247–1251; Gelderblom WCA, Semple E, Marasas WFO, Farber E (1992) "The Cancer-Initiating Potential of the Fumonisin-B Mycotoxins." Carcinogenesis 13:433–437). Fusarium isolates in section Liseola produce fumonisins in culture at levels from 2 to>4000 ppm (Leslie J, Plattner R, Desjardins A, Klittich C (1992) "Fumonisin B1 production by strains from different mating populations of *Gibberella fujikoroi* (Fusarium section Liseola)." Phytopathology 82:341–345). Isolates from maize (predominantly mating population A ) are among the highest producers (Leslie et al., supra). Fumonisin levels detected in field-grown maize have fluctuated widely depending on location and growing season, but both preharvest and postharvest surveys of field maize have indicated that the potential for high levels of fumonisins exists (Murphy P A, Rice L G, Ross P F (1993) "Fumonisin-B1, Fumonisin-B2, and Fumonisin-B3 content of Iowa, Wisconsin, and Illinois corn and corn screenings." J Agr Food Chem 41:263–266). Surveys of food and feed products have also detected fumonisin (Holcomb M, Thompson H C Jr., Hankins L J (1993) "Analysis of fumonisin B-1 in rodent feed by gradient elution HPLC using precolumn derivation with FMOC and fluorescence detection." J Agr Food Chem 41:764–767; Hopmans E C, Murphy P A (1993) "Detection of Fumonisin-B(1), Fumonisin-B(2), and Fumonisin-B(3) and hydrolyzed Fumonisin-B(1) in Corn-Containing foods." J Agr Food Chem 41:1655–1658; Sydenham E W, Shephard G S, Thiel P G, Marasas W F O, Stockenstrom S (1991) "Fumonisin Contamination of Commercial Corn-Based Human Foodstuffs." J Agr Food Chem 39:2014–2018). The etiology of Fusarium ear mold is poorly understood, although physical damage to the ear and certain environmental conditions can contribute to its occurrence(Nelson P E (1992) "Taxonomy and Biology of *Fusarium moniliforme*." Mycopathologia 117:29–36). Fusarium can be isolated from most field grown maize, even when no visible mold is present. The relationship between seedling infection and stalk and ear diseases caused by Fusarium is not clear. Genetic resistance to visible kernel mold has been identified (Gendloff E, Rossman E, Casale W, Isleib T, Hart P (1986) "Components of resistance to Fusarium ear rot in field corn." Phytopathology 76:684–688; Holley R N, Hamilton P B, Goodman M M (1989) "Evaluation of tropical maize germplasm for resistance to kernel colonization by *Fusarium moniliforme*." *Plant Dis* 73:578–580), but the relationship to visible mold to fumonisin production has yet to be elucidated.

Fumonisins have been shown in in vitro mammalian cell studies to inhibit sphingolipid biosynthesis through inhibition of the enzyme sphinganine acyl transferase (Norred W P, Wang E, Yoo H, Riley R T, Merrill A H (1992)"In vitro toxicology of fumonisins and the mechanistic implications." Mycopathologia 117:73–78; Wang E, Norred W, Bacon C, Riley R, Merrill A Jr. (1991) "Inhibition of sphingolipid biosynthesis by fumonisins: implications for diseases associated with *Fusarium moniliforme*." J Biol Chem 266:14486; Yoo H S, Norred W P, Wang E, Merrill A H, Riley R T (1992) "Fumonisin Inhibition of de Novo Sphingolipid Biosynthesis and Cytotoxicity Are Correlated in LLC-PK1 Cells." Toxicol Appl Pharmacol 114:9–15), resulting in the accumulation of the precursor sphinganine. It is likely that inhibition of this pathway accounts for at least some of fumonisin's toxicity, and support for this comes from measures of sphinganine:sphingosine ratios in animals fed purified fumonisin (Wang E, Ross P F, Wilson T M, Riley R T, Merrill A H (1992) "Increases in Serum Sphingosine and Sphinganine and Decreases in Complex Sphingolipids in Ponies Given Feed Containing Fumonisins, Mycotoxins Produced by *Fusarium moniliforme*." J Nutr 122:1706–1716). Fumonisins also affect plant cell growth. (Abbas H K, Boyette C D (1992) "Phytotoxicity of fumonisin B₁ on weed and crop species." Weed Technol 6:548–552; Vanasch M A J, Rijkenberg F H J, Coutinho T A (1992) "Phytotoxicity of fumonisin B₁, moniliformin, and t-2 toxin to corn callus cultures." Phytopathology 82:1330–1332; Vesonder R F, Peterson R E, Labeda D, Abbas H K (1992) "Comparative phytotoxicity of the fumonisins, AAL-Toxin and yeast sphingolipids in *Lemna minorL.* (Duckweed)." Arch Environ Contain Toxicol 23:464–467). Kuti et al. "Effect of fumonisin B₁ on virulence of Fusarium species isolated from tomato plants." (Abstract, Annual Meeting American Phytopathological Society, Memphis, Tenn.: APS Press 1993) reported on the ability of exogenously added fumonisins to accelerate disease development and increase sporulation of *Fusarium moniliforme* and *F. oxysporum* on tomato.

The toxicity of fumonisins and their potential widespread occurrence in food and feed makes it imperative to find detoxification or elimination strategies to remove the compound from the food chain.

DISCLOSURE OF THE INVENTION

The present invention is based on the discovery of organisms with the ability to degrade the mycotoxin fumonisin. In a search for a biological means of detoxifying fumonisins, we have isolated from field-grown maize kernels several dematiaceous hyphomycetes capable of growing on fumonisin B₁ or B₂ (FB₁ or FB₂) as a sole carbon source, degrading it partially or completely in the process. One species, identified as *Exophiala spinifera*, a "black yeast", was recovered from maize seed from diverse locations in the southeastern and south central U.S. A related species, *Rhinocladiella atrovirens*, was isolated from seed originating in both Iowa and Georgia. We also isolated a bacterium, believed to be a Xanthomonas or Sphingomonas species, designated isolate 2412.1, from a field-grown maize stalk sample. This bacterium also showed growth on FB₁ as a sole carbon source, and since its taxonomy is not certain we have deposited the strain with the American Type Culture Collection (ATCC) and it is referred to herein by its ATCC deposit number, 55552. We have also deposited enzyme-active strains of *Exophiala spinifera* (ATCC 74269) and *Rhinocladiella atrovirens* (ATCC 74270).

Deposit Statement

Applicants have made available to the public without restriction deposits with the American Type Culture Collection (ATCC), Rockville, Md. 20852 USA, ATCC Deposit Nos. 74269, 74270, 55552. The deposits with the ATCC are taken from the same deposits maintained by Pioneer Hi-Bred International, Inc., 7100 NW 62$^{nd}$ Avenue, P.O. Box 1000, Johnston, Iowa 50131 since prior to the filing date of this application. Each of these deposits will be maintained without restriction in the ATCC depository, which is a public depository, for a period of 30 years, and at least 5 years after the most recent request, or for the effective life of the patent, whichever is longer, and will be replaced if it becomes nonviable during that period.

All isolates showed the capability to degrade FB₁ in liquid culture. By "degrade" is simply meant that the enzyme is capable of using fumonisin as a substrate and converting it to a different chemical structure. However, our studies indicate that the resulting compounds are less toxic than the fumonisins themselves.

Overall, only 16 of 70 independent seed samples tested yielded degraders. However, several *E. spinifera* isolates, collected outside the U.S. from non-maize sources, were also found to metabolize fumonisins. Representative isolates of other Exophiala species tested (*E. jeanselmi, E. salmonis, E. piscifera*) did not degrade fumonisins, nor did non-maize Rhinocladiella isolates, including *R. atrovirens* and *R. anceps*, nor fungi associated with ear molds including *Fusarium moniliforme, F. graminearum, Aspergillus flavus* and *Diplodia maydis*. Fumonisin-metabolizing black yeasts were found to possess an inducible hydrolase activity that cleaves the tricarballylate esters of FB₁, as monitored by C₁₈-thin layer chromatography (TLC) and fluorescence detection of amines. The identity of the resulting amino alcohol compound, designated AP₁, was verified by FAB-mass spectroscopy. The latter compound has utility as a chemical indicator of fumonisin metabolism. *E. spinifera* cultures further metabolized AP₁ to compounds of unknown identity that were not detectable by amine reagents on TLC. Crude, cell-free culture filtrates of the *E. spinifera* isolate designated 2141.10 contained a heat-labile, protease-sensitive hydrolase activity attributed to an enzyme tentatively characterized as an esterase with specificity for tricarballylate esters of fumonisins and similar molecules such as AAL-toxin from *Alternaria alternata lycopersici*. This purified esterase is believed to be a new chemical entity, since no commercially available esterases tested were able to hydrolyze the tricarballylate esters of FB₁, suggesting a novel enzyme specificity produced by these fungi. These enzymes and genes coding for these enzymes, being involved in fumonisin degradation, have utility in detoxification of maize seed pre- or post-harvest.

DETAILED DESCRIPTION OF THE INVENTION

This invention provides newly discovered enzymes capable of degrading and detoxifying fumonisins, produced by fermentation of one or more of *Exophiala spinifera*, ATCC 74269, *Rhinocladiella atrovirens*, ATCC 74270, or the bacterium of ATCC 55552. The invention further comprises methods for making enzymes that are capable of detoxifying fumonisins, comprising the step of growing one or more of *Exophiala spinifera*, ATCC 74269, *Rhinocladiella atrovirens*, ATCC 74270, or the bacterium ATCC 55552 in the presence of a fumonisin or the metabolite produced by action of the enzyme on a fumonisin. This invention further provides methods of detoxifying fumonisins, comprising the step of reacting them with an enzyme derived from *Exophiala spinifera*, ATCC 74269, *Rhinocladiella atrovirens*, ATCC 74270, or the bacterium of ATCC 55552.

We have isolated and sequenced the gene that codes for the fumonisin-degrading enzyme from one of these organisms and provide the amino acid sequence of the enzyme here. It is known that genes encoding desired proteins can be identified, isolated, cloned and expressed in transgenic organisms, including several important crop plants. One commonly used method of gene transfer in plants involves the use of a disarmed form of the Ti plasmid of the soil bacterium *Agrobacterium tumefaciens*. *A. tumefaciens* is a plant pathogen that causes crown-gall tumors in infected plants. Large plasmids, termed Ti- or tumor-inducing plasmids, are responsible for the oncogenicity of the bacterium as well as for the transfer of foreign DNA to the plant. Similarly, *A. rhizogenes* contains Ri-or root-inducing plasmids that induce root growth. Both plasmid types include a vir or virulence region that must be functional in order to transform wild-type cells to tumor cells.

Transformation results in the integration of another plasmid portion, termed the T- or transfer-DNA, into the nuclear genome of the transformed cells. Ri and Ti plasmids can be manipulated to allow insertion of foreign DNA, encoding a desired protein, into the T-DNA region. The foreign DNA can be transferred either via a vector bearing both the vir gene and the foreign gene or by a binary vector system consisting of two plasmids, one containing the vir gene and the other carrying the foreign gene. See, e.g., U.S. Pat. No. 4,658,082. Transformed plant cells can then be regenerated to produce varieties bearing the inserted gene. The production of transgenic, fumonisin-resistant plants will provide a useful and novel approach for the control of Fusarium-induced plant diseases.

This invention also provides a mechanism for selection of transformants: growth of plant cells in the presence of a Fusarium or its mycotoxin favors the survival of plant cells that have been transformed to express the coding sequence that codes for the enzyme of this invention and degrade the toxin. Thus, the coding sequence that codes for the enzyme of this invention can itself be used as a selectable marker, or as a scorable marker by measuring formation of the amino alcohol metabolite.

Another embodiment of the present invention is directed to a DNA construct comprising an expression cassette comprised of:

a) a DNA coding sequence for a polypeptide capable of degrading fumonisin; and b) control sequences that are operably linked to the coding sequence whereby the coding sequence can be transcribed and translated in a host cell, and at least one of the DNA coding sequences or control sequences is heterologous to the host cell.

Preferred embodiments of the subject invention include a host cell stably transformed by a DNA construct as described above; and a method of producing a polypeptide of a recombinant gene comprising:

a) providing a population of these host cells; and b) Vowing the population of cells under conditions whereby the polypeptide encoded by the coding sequence of the expression cassette is expressed.

In yet another embodiment, the present invention is directed to a transgenic plant capable of degrading fumonisin. In another embodiment, the transgenic plant is a maize plant capable of degrading fumonisin.

Another embodiment of the subject invention comprises a method of conferring fumonisin-resistance to a plant substantially without such resistance comprising transferring to the plant an expressible gene encoding a polypeptide capable of degrading fumonisin.

Thus, DNA encoding a protein able to inactivate fumonisin can be isolated and cloned in an appropriate vector and inserted into an organism normally sensitive to the Fusarium or its toxin. Organisms expressing the gene can be easily identified by their ability to degrade fumonisin. The protein capable of degrading fumonisin can be isolated and characterized using techniques well known in the art. Furthermore, the gene imparting fumonisin-resistance can be transferred into a suitable plasmid, such as into the T-DNA region of the Ti or Ri plasmid of the soil bacteria *Agrobacterium tumefaciens* or *Agrobacterium rhizogenes*, respectively. Plant tissue can be inoculated with the transformed bacteria. Additionally, plant tissues which have been co-cultivated with *Agrobacterium spp*. can be incubated in the presence of fumonisin to select for fumonisin-degrading transgenic plants, i.e., the gene for fumonisin degradation can serve as a selectable marker. Thus, the inoculated tissue is regenerated to produce fumonisin-degrading transgenic plants.

INDUSTRIAL APPLICABILITY

The practice of the present invention will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g., J. H. Langenheim and K. V. Thimann, Botany: Plant Biology and Its Relation to Human Affairs (1982) John Wiley; Cell Culture and Somatic Cell Genetics of Plants, Vol. 1 (I. K. Vasil, ed. 1984); R. V. Stanier, J. L. Ingraham, M. L. Wheelis, and P. R. Painter, The Microbial World, (1986) 5th Ed., Prentice-Hall; O. D. Dhringra and J. B. Sinclair, Basic Plant Pathology Methods, (1985) CRC Press; Maniatis, Fritsch & Sambrook, Molecular Cloning: A Laboratory Manual (1982); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); and the series Methods in Enzymology (S. Colowick and N. Kaplan, eds., Academic Press, Inc.).

In describing the present invention, the following terms will be employed, and are intended to be defined as indicated below.

By "microbe" is meant any microorganism (including both eucaryotic and procaryotic microorganisms), such as fungi, yeasts, bacteria, actinomycetes, algae and protozoa, as well as other unicellular structures capable of growth in culture.

A "fumonisin-producing microbe" is any microbe capable of producing the mycotoxin fumonisin or analogs thereof. Such microbes are generally members of the fungal. genus Fusarium, as well as recombinantly derived organisms which have been genetically altered to enable them to produce fumonisin or analogues thereof.

By "degrading fumonisin" is meant any modification to the fumonisin molecule which causes a decrease or loss in its toxic activity. Such a change can comprise cleavage of any of the various bonds, oxidation, reduction, the addition or deletion of a chemical moiety, or any other change that affects the activity of the molecule. In a preferred embodiment, the modification includes lysis of the ester linkage in the molecule as a first step. Furthermore, chemically altered fumonisin can be isolated from cultures of microbes that produce an enzyme of this invention, such as by growing the organisms on media containing radioactively-labeled fumonisin, tracing the label, and isolating the degraded toxin for further study. The degraded fumonisin can be compared to the active compound for its phytotoxicity or mammalian toxicity in known sensitive species, such as bovines and equines. Such toxicity assays are known in the art. For example, in plants a whole leaf bioassay can be used in which solutions of the active and inactive compound are applied to the leaves of sensitive plants. The leaves may be treated in situ or, alternatively, excised leaves may be used. The relative toxicity of the compounds can be estimated by grading the ensuing damage to the plant tissues and by measuring the size of lesions formed within a given time period. Other known assays can be performed at the cellular level, employing standard tissue culture methodologies e.g., using cell suspension cultures.

By "transgenic plant" is meant any plant or plant cell that has become transformed by the introduction, stable and heritable incorporation, into the subject plant or plant cell, of foreign DNA, i.e. DNA encoding for a protein not normally found within that plant species.

"Plantlet" refers to a plant sufficiently developed to have a shoot and a root that is asexually reproduced by cell culture.

"Explant" refers to a section or piece of tissue from any part of a plant for culturing.

By "hormone" is meant any plant growth regulator that affects the growth or differentiation of plant cells. Such hormones include cytokinins, auxins, and gibberellins, as well as other substances capable of affecting plant cells.

The term "callus" and its plural "calli", refer to an unorganized group of cells formed in response to cutting, severing, or other injury inflicted on plant tissue. Excised pieces of plant tissue and isolated cells can be induced to form callus under the appropriate culture conditions. Callus can be maintained in culture for a considerable time by transferring or subculturing pans of the callus to fresh medium at regular intervals. The transfer of callus to liquid medium leads to dispersion of the tissue and the formation of a plant cell suspension culture. Callus can be induced to undergo organized development to form shoots and roots.

"Embryoid" refers to a structure similar in appearance to a plant zygotic embryo.

"Somatic hybrid" and "somatic hybridization" refers generally to stable combination of cellular material, be it protoplast/protoplast or protoplast/cytoplast combinations, and includes cybrids and cybridization.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage, or cosmid, to which another DNA segment may be attached so as to bring about the replication of the attached segment.

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA, eucaryotic mRNA, genomic DNA sequences from eucaryotic (e.g., mammalian) DNA, and even synthetic DNA sequences. A polyadenylation signal and transcription termination sequence will usually be located 3' to the coding sequence.

A "promoter sequence" is a DNA regulatory region capable of binding RNA polymerase in a cell and initiating transcription of a downstream (3' direction) coding sequence. For purposes of defining the present invention, the promoter sequence is bound at its 3' terminus by the translation start codon (ATG) of a coding sequence and extends upstream (5' direction) to include the minimum number of bases or elements necessary to initiate transcription. Within the promoter sequence will be found a transcription initiation site, as well as protein binding domains responsible for the binding of RNA polymerase. Eucaryotic promoters will often, but not always, contain "TATA" boxes and "CAT" boxes. Procaryotic promoters contain Shine-Dalgarno sequences.

DNA "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell.

A coding sequence is "operably linked to" or "under the control of" control sequences in a cell when RNA polymerase will bind the promoter sequence and transcribe the coding sequence into mRNA, which is then translated into the polypeptide encoded by the coding sequence.

A "host cell" is a cell which has been transformed, or is capable of undergoing transformation, by an exogenous DNA sequence.

A cell has been "transformed" by exogenous DNA when such exogenous DNA has been introduced inside the cell membrane. Exogenous DNA may or may not be integrated into (covalently linked to) chromosomal DNA making up the genome of the transformed cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA.

A "clone" is a population of cells derived from a single cell or common ancestor by mitosis. A "cell line" is a clone of a primary cell that is capable of stable growth in vitro for many generations.

Two DNA, RNA or polypeptide sequences are "substantially homologous" when at least about 85% (preferably at least about 90%, and most preferably at least about 95%) of the nucleotides or amino acids match over a defined length of the molecule. DNA sequences that are substantially homologous can be identified in a Southern hybridization experiment under, for example, stringent conditions, as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacterium. Another example of a heterologous coding sequence is a construct where the coding sequence itself is not found in nature (e.g., synthetic sequences having codons different from the native gene). "Heterologous" DNA also refers to DNA not found within the host cell in nature. Allelic variation or naturally occurring mutational events do not give rise to a heterologous region of DNA, as these terms are used herein.

The term "polypeptide" as used herein is used in its broadest sense, i.e., any polymer of amino acids (dipeptide or greater) linked through peptide bonds. Thus, the term "polypeptide" includes proteins, oligopeptides, protein fragments, analogues, muteins, fusion proteins and the like. The term also encompasses amino acid polymers as described above that include additional non-amino acid moieties. Thus, the term "polypeptide" includes glycoproteins, lipoproteins, phosphoproteins, metalloproteins, nucleoproteins, as well as other conjugated proteins. The term "polypeptide" contemplates polypeptides as defined above that are recombinantly produced, isolated from an appropriate source, or synthesized.

This invention can be better understood by reference to the following non-limiting examples. It will be appreciated by those skilled in the art that other embodiments of the invention may be practiced without departing from the spirit and the scope of the invention as herein disclosed and claimed.

EXAMPLE 1

Chemicals and Reagents

All chemicals were reagent grade or better unless otherwise indicated. Fumonisin $B_1$ and $B_2$ were obtained from Sigma Chemical Co. Partially purified fumonisins (eluate from C8 column) were obtained from Dr. Pat Murphy (Iowa State University). AAL-toxin (TA isomer) was a gift of Dr. David Gilchrist (University of California-Davis).

Plant Tissue Samples

Mature, field-grown maize seed was obtained from maize breeding locations of Pioneer Hi-Bred International, Inc. in the Southeast, Midwest and South Central regions of the U.S. Seed was stored at room temperature in individual packets.

Fungal and Bacterial Isolates

Exophiala and Rhinocladiella isolates from maize were isolated as described below. Other isolates were obtained from Dr. C. J. Wang (Syracuse, N.Y.), Dr. Michael McGinnis (Case Western Reserve University, Cleveland, Ohio), and from the American Type Culture Collection (Bethesda, Md.). *Fusarium graminearum* [*Gibberella zeae* (Schw.) Petsch], *Diplodia maydis*, and *Fusarium moniliforme* Sheld., were obtained from the microbial culture collection of Pioneer Hi-Bred International, Inc. *Aspergillus flavus* (Schw.) Petsch, isolate CP22, was obtained from Don Sumner at the University of Georgia (Tifton, Ga.). *Xanthomonas sp.* 2412.1 was isolated from maize stalk tissue as described below.

Isolation Methods

Individual kernels, either intact or split in two with a sterile razor blade, were rinsed for 1 hr in 5 ml sterile water with agitation. From 1 to 5 µl of the rinse fluid was added to 100 µL of sterile, carbon-free mineral salts medium +$FB_1$ (MS-$FB_1$) (1 g/liter $NH_3SO_4$, 1 g/liter $K_2HPO_4$, 1 g/liter NaCl, 0.2 g/liter $MgSO_4 \cdot 7H_2O$, pH 7.0) containing $FB_1$ (Sigma Chemical Co.) at 0.5 to 1.0 mg/ml). The pH of the medium was approx. 6.0 after addition of $FB_1$. After 1 to 2 weeks incubation at 28° C. in the dark, serial 10-fold dilutions were made in sterile $dH_2O$, and aliquots were plated onto 1.2% Bacto-agar containing 0.1% yeast extract, 1% Bacto-peptone and 0.1% dextrose (YPD agar). Fungal and bacterial colonies that appeared on agar were transferred onto fresh plates and individual colonies were evaluated for fumonisin metabolizing ability by inoculating them into fresh MS—$FB_1$. Loss of fumonisin from the medium was monitored periodically by spotting 0.5 to 1 microliter aliquots of culture supernatant on $C_{18}$ silica gel plates that were then air-dried and developed as described below (see Analysis of fumonisins and metabolism products).

Direct isolation of black yeasts from seed was accomplished by plating 100 microliters of seed wash fluid onto YPD or Sabouraud agar augmented with cycloheximide (500 rag/liter) and chloramphenicol (50 mg/liter). Plates were incubated at room temperature for 7–14 days, and individual pigmented colonies that arose were counted and cultured for analysis of fumonisin-degrading ability as described above.

For stalk isolations, mature stalk samples 0.5×0.5×2 cm were taken from Southern-type maize inbreds grown in Johnston, Iowa by Pioneer Hi-Bred International, Inc., a seed company, in 1993. One-inch sections of the center (pith) or the outside of non-surface-sterilized stalk were cut and placed in 10 mi. sterile water in a small, sterilized tube. The tubes were shaken for 1 hour, and then 2 µl of washate were withdrawn and used to inoculate 100 µl of MS—$FB_1$ in a microtiter plate. Subsequent steps were as above.

Analysis of Fumonisins and Metabolism Products

Analytical thin-layer chromatography was carried out on 100% silanized $C_{18}$ silica plates (Sigma™ #T-7020; 10×10 cm; 0.1 mm thick) by a modification of the published method of Rottinghaus. Sample lanes were pre-wet with methanol to facilitate sample application. After application of from 0.1 to 2 µl of aqueous sample, the plates were air-dried and developed in MeOH:4% KCl (3:2) or MeOH:0.2M KOH (3:2) and then sprayed successively with 0.1M sodium borate (pH 9.5) and fluorescamine (0.4 mg/ml in acetonitrile). Plates were air-dried and viewed under long wave UV.

Alkaline Hydrolysis of $FB_1$ to $AP_1$.

$FB_1$ or crude fumonisin $C_8$ material was suspended in water at 10–100 mg/ml and added to an equal volume of 4N NaOH in a screw-cap tube. The tube was sealed and incubated at 60° C. for 1 hr. The hydrolysate was cooled to RT and mixed with an equal volume of ethyl acetate, centrifuged at 1000 RCF for 5 minute and the organic (upper) layer recovered. The pooled ethyl acetate layers from two successive extractions were dried under $N_2$ and resuspended in $dH_2O$. The resulting material (the aminopentol of $FB_1$ or "$AP_1$") was analyzed by TLC.

Tables 1 and 2 illustrate the results of efforts to isolate a fumonisin-degrading enzyme from a wide assortment of sources. As is noted, *E. spinifera* isolates from maize seed from various locations were always able to produce a fumonisin-degrading enzyme when grown on fumonisin as a sole carbon source (Table 1), as were *E. spinifera* isolates from other sources from around the world (Table 2). Some samples of *Rhinocladiella atrovirens* from maize seed were also able to produce this enzyme (Table 1). Other species of Exophiala and other sources and species of Rhinocladiella were routinely unable to produce the enzyme, even when isolated from plant-related sources (Table 2).

TABLE 1

Dematiaceous fungi isolated from maize seed that degrade fumonisin

| | | | | | Modification of substrates | |
|---|---|---|---|---|---|---|
| Isolate# | Species | Location of origin | Isolated from | Appear-ance[1] | $FB_1$ | $AP_1$ |
| 2369.E7 | Exophiala spinifera | Tifton, GA | Maize seed (3293) | clean | + | + |
| 2369.G5 | Exophiala spinifera | Tifton, GA | Maize seed (3379) | clean | + | + |
| 2174.A4 | Exophiala spinifera | Tifton, GA | Maize seed (inbred) | moldy | + | + |
| 2369.F7 | Exophiala spinifera | Winterville, NC | Maize seed (3170) | moldy | + | + |
| 2369.H9 | Exophiala spinifera | Winterville, NC | Maize seed (3379) | moldy | + | + |
| 2141.10 | Exophiala spinifera | Winterville, NC | Maize seed (unk) | moldy | + | + |
| 2174.C6 | Rhinocladiella atrovirens | Winterville, NC | Maize seed (unk) | moldy | + | + |
| 2170.2 | Exophiala spinifera | Winterville, NC | Maize seed (inbred) | moldy | + | + |
| 2174.A4 | Exophiala spinifera | Union City, TN | Maize seed (inbred) | moldy | + | + |
| 2219.H5 | Exophiala spinifera | Union City, TN | Maize seed (inbred) | moldy | + | + |
| 2363.1 | Exophiala spinifera | Weslaco, TX | Maize seed (inbred) | moldy | + | + |
| 2363.3 | Exophiala spinifera | Weslaco, TX | Maize seed (inbred) | moldy | + | + |

TABLE 1-continued

Dematiaceous fungi isolated from maize seed that degrade fumonisin

| Isolate# | Species | Location of origin | Isolated from | Appearance[1] | Modification of substrates FB$_1$ | AP$_1$ |
|---|---|---|---|---|---|---|
| 2363.3 | Exophiala spinifera | Weslaco, TX | Maize seed (inbred) | moldy | + | + |
| 2363.8 | Exophiala spinifera | Weslaco, TX | Maize seed (inbred) | moldy | + | + |
| 2363.10 | Exophiala spinifera | Weslaco, TX | Maize seed (inbred) | moldy | nt | |
| 2369.F11 | Rhinocladiella atrovirens | Johnston, IA | Maize seed (inbred) | clean | + | + |

[1]"moldy" implies visible discoloration of kernel pericarp, cracking or splitting; "clean" implies no visible signs of infection on the kernel
[2]Evaluated by TLC analysis of culture supernatants as described herein nt = not tested.

TABLE 2

Other fungal isolates tested for degradation of fumonisin B1 in liquid culture

| Isolate | Species | Source | Location of Origin | Isolated from | Modification of substrates FB$_1$ | AP$_1$ |
|---|---|---|---|---|---|---|
| | | | Yeast Fungi | | | |
| 26089 | Exophiala spinifera | ATCC | Uruguay | Palm trunk | + | + |
| 26090 | Exophiala spinifera | ATCC | Uruguay | Palm tree fruit | + | + |
| 26091 | Exophiala spinifera | ATCC | Uruguay | Bird's nest | –? | nt |
| 26092 | Exophiala spinifera | ATCC | Uruguay | Bird's nest | + | + |
| 48173 | Exophiala spinifera | ATCC | | Nasal Granuloma | + | + |
| 56567 | Exophiala spinifera | ATCC | | ? | + | + |
| 18218 | Exophiala spinifera | ATCC | | Nasal Granuloma | + | + |
| 58092 | Exophiala spinifera | ATCC | | Human | + | + |
| 66775 | Exophiala monileae | ATCC | | | – | nt |
| 32288 | Exophiala salmonis | ATCC | Unknown | Leaf Litter | – | nt |
| 26438 | Exophiala pisciphila | ATCC | Australia | Wheat rhizosphere | – | nt |
| 26272 | Exophiala jeanselmi | ATCC | Canada | Activated sludge | – | nt |
| P-154 | Rhinocladiella atrovirens | C.J. Wang | Chester, NJ | Southern pine pole | – | nt |
| P-330 | Rhinocladiella atrovirens | C.J. Wang | Binghamton, NY | Southern pine pole | – | nt |
| P-646 | Rhinocladiella atrovirens | C.J Wang | Virginia | Southern pine pole | – | nt |
| P-1492 | Rhinocladiella atrovirens | C.J. Wang | Chester, NJ | Southern pine pole | – | nt |
| ED-43 | Rhinocladiella atrovirens | C.J Wang | Unknown | Douglas-fir pole | – | nt |
| ED-124 | Rhinocladiella atrovirens | C.J Wang | Unknown | Douglas-fir pole | – | nt |
| 28220 | Rhinocladiella anceps | ATCC | Maryland- | Grass | – | nt |

TABLE 2-continued

Other fungal isolates tested for degradation of fumonisin B1 in liquid culture

| Isolate | Species | Source | Location of Origin | Isolated from | Modification of substrates FB$_1$ | AP$_1$ |
|---|---|---|---|---|---|---|
| *Ear mold fungi* | | | | | | |
| FMO001 | Fusarium moniliforme | PHI | Unknown | Maize | – | nt |
| FGR001 | Fusarium graminearum | PHI | Unknown | Maize | – | nt |
| CP22 | Aspergillus flavus | PHI | Unknown | Maize | – | nt |
| DMA001 | Diplodia maydis | PHI | Unknown | Maize | – | nt |

*Tested both with FB$_1$ and as a sole carbon source and with FB$_1$ amended with 1% sucrose.

TABLE 3

Frequency of isolation of fumonisin-degrading black yeast isolates from maize seed

| Location of origin | # samples tested | # samples positive | % containing FB$_1$-degrading black yeast | Species identified |
|---|---|---|---|---|
| Weslaco, TX | 8 | 6 | 75.0 | Exophiala spinifera |
| Winterville, NC | 19 | 4 | 47.5 | Exophiala spinifera, Rhinocladiella atrovirens |
| Tifton, GA | 8 | 3 | 37.5 | Exophiala spinifera |
| Union City, TN | 7 | 2 | 28.2 | Exophiala spinifera |
| Johnston, IA | 7 | 1 | 14.3 | Rhinocladiella atrovirens |
| Shelbyville, IL | 3 | 0 | 0 | none |
| Macomb, IL | 4 | 0 | 0 | — |
| Champaign, IL | 3 | 0 | 0 | — |
| Yale, IN | 3 | 0 | 0 | — |
| California | 8 | 0 | 0 | — |
| Total | 70 | 16 | 22.8 | |

Organisms can be screened for their ability to degrade fumonisin using the present methods. In this way, plant, soil, marine and fresh water samples can be screened and organisms isolated therefrom that are able to degrade fumonisin. Alternatively, already isolated microbial strains that are suspected of possessing this capability can be screened. Putative fumonisin-resistant bacteria include bacteria associated with plant species susceptible to Fusarium infection. For instance, bacteria associated with Fusarium-infected tomato and pepper as well as other susceptible plant species, might be expected to degrade fumonisin. Furthermore, members of bacterial genera known to be versatile in their catabolism of complex organic molecules, such as members of the genus Pseudomonas, might degrade fumonisin.

Generally, media used to culture the above microbes will contain a known amount of fumonisin, i.e. from 0.1 to 3 mg of fumonisin per ml of media, more usually from 0.25 to 2 mg per ml of media, and preferably from 0.5 to 1 mg of fumonisin per ml of media.

A further study was performed to determine if colony morphology could be used to determine which strains of these species would produce a fumonisin-degrading enzyme. The results as shown in Table 4 indicated that *E. spinifera* and *R. atrovirens* colonies having different morphologies could nevertheless produce the fumonisin-degrading enzyme.

TABLE 4

Black yeasts recovered from a single kernel by direct plating seed washates onto YPD + cycloheximide + chloramphenicol[1]

| Isolate | Colony Type on YPD agar | Species | # colonies | # FB$_1$ degr |
|---|---|---|---|---|
| 2403.5 | Light brown, shiny | Exophiala spinifera | 33 | 33 |
| 2403.25 | Dark brown, shiny | Exophiala spinifera | 1 | 1 |
| 2403.12 | Brown, velvety | Rhinocladiella atrovirens | 4 | 4 |
| 2403.2 | Grey, velvety | Rhinocladiella atrovirens | 1 | 1 |
| Totals | | | 39 | 39 |

[1]Kernel source: Tifton, Georgia. Seed was split, washed in 5 ml sterile water and then 100 ul was plated onto YPD agar containing cycloheximide (500 mg/L) and chloramphenicol (50 mg/L).

From these results it was concluded that growth on fumonisin as the sole carbon source is the most reliable indicator of the ability to produce the fumonisin-degrading esterase.

The esterase isolated from *E. spinifera* was then subjected to other treatments, including proteases, to determine whether and how the enzyme would function in various environments. The results are indicated in Table 5.

TABLE 5

Effect of various treatments on modification of $FB_1$

| Treatment | Conditions | $FB_1$ Hydrolase activity* |
|---|---|---|
| Control | 16 hr, 37° C., pH 5.2 | +++ |
| Boiling water bath | 100° C., 30 min, pH 5.2 | − |
| Protease K | 0.01 mg/ml, 16 hr, 37° C., pH 5.2 | + |
| Pronase E | 0.01 mg/ml, 16 hr, 37° C., pH 5.2 | ++ |
| Chymotrypsin | 0.01 mg/ml, 16 hr, 37° C., pH 5.2 | ++ |
| Trypsin | 0.01 mg/ml, 16 hr, 37° C., pH 5.2 | +++ |
| EDTA | 50 mM | ++ |
| DTT | 25 mM | +++ |
| $Ca^{++}$ | 50 mM | +++ |
| $Mg^{++}$ | 50 mM | +++ |
| PMSF | 10 mM | +++ |

*10-fold concentrated, 11 to 15 day culture filtrates treated as described and then incubated with $FB_1$ (0.5 mg/ml final conc) overnight at 37° C. Analysis by $C_{18}$ TLC/fluorescamine spray following overnight incubation at 37° C. with 1 mg/ml fumonisin
− = no hydrolysis
± = trace amount of hydrolysis
+ = incomplete hydrolysis
++ = incomplete hydrolysis
+++ = complete hydrolysis Next, the pH range of activity of the fumonisin esterase was evaluated by measuring fumonisin degradation in the presence of citrate and citrate-phosphate buffers at varying pH levels. Results are shown in Table 6. From this, it was concluded that the pH range of the enzyme was quite wide, and that the enzyme would function at the internal pH of plants and plant cells.

TABLE 6

Effect of buffer pH on hydrolysis of fumonisin $B_1$ by *E. spinifera* culture filtrate

| Buffer | pH | $FB_1$ Hydrolase activity* |
|---|---|---|
| 0.1 M citrate | 3.0 | +++ |
| 0.1 M citrate-phosphate | 4.0 | +++ |
| 0.1 M citrate-phosphate | 5.0 | ++ |
| 0.1 M citrate-phosphate | 6.0 | ++ |
| 0.1 M phosphate | 7.0 | ± |
| 0.1 M phosphate | 8.0 | − |

*reactions were carried out at 37° C. overnight and then assayed by TLC
*Analysis by $C_{18}$ TLC/fluorescamine spray following overnight incubation at 37° C. with 1 mg/ml fumonisin.
− = no hydrolysis
± = trace amount of hydrolysis
+ = incomplete hydrolysis
++ = incomplete hydrolysis
+++ = complete hydrolysis..

The fumonisin esterase isolated from *E. spinifera* and *R. atrovirens* was compared with other known esterases from various sources as supplied by commercial vendors. The results shown in Table 7 indicate that the fumonisin esterase is a unique enzyme that is highly specific in its activity and does not have a generalized esterase activity comparable to that of any of the known enzymes tested.

TABLE 7

Hydrolysis of fumonisin $B_1$ by commercial esterases and hydrolases

| Enzyme | Code | Source, purity | Units/ mg prot. | Units per rxn | Assay pH | $FB_1$ hydrolysis |
|---|---|---|---|---|---|---|
| Esterase, nonspecific | EC 3.1.1.1 | Rabbit | 100 | | 8.0 | − |
| Esterase, nonspecific | EC 3.1.1.1 | Porcine liver | 200 | | 7.5 | − |
| Lipase | EC 3.1.1.3 | *Candida cylindrica* | 35 | | 7.7 | − |
| Cholinesterase, butyryl | EC 3.1.1.8 | Horse serum, highly purified | 500 | 15 | 8.0 | − |
| Cholinesterase, acetyl | EC 3.1.1.7 | Bovine, partially pure | 0.33 | 0.15 | 8.0 | − |
| Cholesterol esterase | EC 3.1.1.13 | Bovine, partially pure | 0.5 | 0.15 | 8.0 | − |
| Cholesterol esterase | EC 3.1.1.13 | Porcine, partially pure | | 0.15 | 8.0 | − |
| Cholesterol esterase | EC 3.1.1.13 | *Pseudomonas fluorescens* | 12 | 1.5 | 7.0 | − |
| Cholesterol esterase, | EC 3.1.1.13 | *Pseudomonas sp.* | 200 | 15 | 7.0 | ± |
| Acetylesterase | EC 3.1.1.6 | Orange Peel partially pure | 4 | 0.15 | 6.5 | ± |
| Pectinesterase | EC 3.1.1.11 | Orange Peel, partially pure | 100 | 1.5 | 7.5 | − |
| Pectinase | EC 3.2.1.15 | *Rhizopus* Crude | 0.5 | 1.5 | 4.0 | − |
| Pectinase | EC 3.2.1.15 | *Aspergillus* Partially pure | 5 | 0.1 | 4.0 | − |
| Fumonisin esterase | ? | *Exophiala spinifera*, crude | unk | .001 | 5.2 | +++ |

*Analysis by $C_{18}$ TLC/fluorescamine spray following overnight incubation at 37° C. with 1 mg/ml fumonisin.
− = no hydrolysis
± = trace amount of hydrolysis

TABLE 7-continued

Hydrolysis of fumonisin $B_1$ by commercial esterases and hydrolases

| Enzyme | Code | Source, purity | Units/ mg prot. | Units per rxn | Assay pH | $FB_1$ hydrolysis |
|---|---|---|---|---|---|---|

+ = incomplete hydrolysis
++ = incomplete hydrolysis
+++ = complete hydrolysis

The enzyme of this invention was evaluated for inducibility by growing an Exophiala culture on various carbon sources of varying degrees of structural similarity to fumonisin. The results, shown in Table 8, illustrate that both the original form of fumonisin and its metabolite are capable of inducing enzyme production, but that inducibility of the enzyme is also quite specific.

TABLE 8

Ability of various carbon sources to support growth and/or induction of $FB_1$ hydrolytic activity Exophiala culture activity

| Carbon source | Concentration | Growth | $FB_1$ hydrolase activity |
|---|---|---|---|
| $FB_1$ | 0.1% | + | + |
| Alkaline hydrolyzed $FB_1$ (AP1) | 0.1% | + | + |
| Na+ Tricarballylate | 0.1% | ± | − |
| Sphingosine | 0.1% | − | − |
| Phytosphingosine | 0.1% | − | − |
| Na+ Citrate | 0.1% | + | − |
| Sucrose | 0.1% | + | − |
| Glucose | 0.1% | + | − |

The ability of the fumonisin esterase to cleave other organic carboxylesters was also evaluated in comparison to its ability to hydrolyse fumonisin. The results, shown in Table 8, also illustrate that the enzyme hydrolyzed the tricarballylates of other related aminoalcohols such as $FB_2$ and AAL toxin.

TABLE 9

Hydrolysis of organic carboxylesters by Exophiala crude concentrated culture filtrate

| Substrate | Conditions | Assay method | Hydrolysis by Exophiala culture filtrate |
|---|---|---|---|
| $FB_1$ | pH 5.2, 37° C. 1 hr | $C_{18}$ TLC: fluorescamine | + |
| FB2 | pH 5.2, 37° C. 1 hr | $C_{18}$ TLC: fluorescamine | + |
| AAL-toxin | pH 5.2, 37° C. 1 hr | $C_{18}$ TLC: fluorescamine | + |

Enzyme Activity of Culture Filtrate and Mycelium

*Exophiala spinifera* isolate 2141.10 was grown on YPD agar for 1 week, and conidia were harvested, suspended in sterile water, and used at 105 conidia per ml to inoculate sterile Fries mineral salts medium containing 1 mg/ml purified $FB_1$ (Sigma Chemical Co.). After 2 weeks incubation at 28° C. in the dark, cultures were filtered through 0.45 micron cellulose acetate filters, and rinsed with Fries mineral salts. Fungal mycelium was suspended in 15 mL of 0. 1 MC-$FB_1$, pH 5.2+1 mM EDTA +3 μg/mL Pepstalin A+1.5 μg/mL Leupeptin and disrupted in a Bead Beater™ using 0.5 mm beads and one minute pulses, with ice cooling. Hyphal pieces were collected by filtering through Spin X (0.22 μm), and both mycelial supernalant and original culture filtrates were assayed for fumonisin modification by methods outlined above.

Preparation of Crude Culture Filtrate

Agar cultures grown as above were used to inoculate YPD broth cultures (500 ml) in conical flasks at a final concentration of 105 cells per ml culture. Cultures were incubated 5 days at 28° C. without agitation and mycelia harvested by filtration through 0.45 micron filters under vacuum. The filtrate was discarded and the mycelial mat was washed and resuspended in sterile carbon-free, low mineral salts medium (1 g/liter $NH_3NO_4$; 1 g/liter $NaH_2PO_4$; 0.5 g/liter $MgCl_2$; 0.1 g/liter NaCl; 0.13 g/liter $CaCl_2$; 0.02 g/liter $FeSO_4 \cdot 7H_2O$, pH 4.5) containing 0.5 mg/ml alkaline hydrolyzed crude $FB_1$. After 3–5 days at 28° C. in the dark with no agitation the cultures were filtered through low protein binding 0.45 micron filters to recover the culture filtrate. Phenylmethyl sulfonyl fluoride (PMSF) was added to a concentration of 2.5 mM and the culture filtrate was concentrated using an Amicon™ YM10 membrane in a stirred cell at room temperature, and resuspended in 50 mM sodium acetate, pH 5.2 containing 10 mM $CaCl_2$. The crude culture filtrate (approx. 200-fold concentrated) was stored at −20° C.

To obtain preparative amounts of enzyme-hydrolyzed fumonisin, 10 mg. of $FB_1$ (Sigma) was dissolved in 20 mL of 50 mM sodium acetate at pH 5.2+10 mM $CaCl_2$, and 0.25 mL of 200× concentrated crude culture filtrate of 2141.10 was added. The solution was incubated at 37° C. for 14 hours, and then cooled to room temperature. The reaction mixture was brought to approx. pH 9.5 by addition of 0.4 mL of 4N KOH, and the mixture was extracted twice with 10 mL ethyl acetate. The combined organic layers were dried under $LN_2$ and resuspended in $dH_2O$. 2.5 milligrams of organic extracted material were analyzed by Fast Atom Bombardment (FAB) mass spectrometry. The resulting mass spectrum showed a major peak at 406 mass units, indicating the major product of enzymatic hydrolysis was $AP_1$, which has a calculated molecular weight of 406.63.

Additional Characterization of Fumonisin Esterases from *Exophiala spinifera* and Gram-negative Bacterium Species Crude, concentrated culture filtrates (induced for $FB_1$ esterase activity) from *E. spinifera* isolate 2141.10 and *Xanthomonas sp.* 2412.1 were chromatographed on a Pharmacia® Superdex 75 size exclusion column and eluted with 50 mM sodium phosphate, pH 6.0 containing 0.2M NaCl. One-mL fractions were collected and assayed for $FB_1$ esterase activity by methods described above. The retention times for the 2141.10 and 2412.1 $FB_1$ esterases resulted in estimated molecular weights of 44.5 and 28.7 kilodaltons, respectively.

Similarly, crude concentrated culture filtrates in 1.7M ammonium sulfate were injected onto a Pharmacia® Phenyl Sepharose FPLC column equilibrated with 1.7M ammonium sulfate in 50 mM sodium phosphate pH 6.0 (Buffer A). A 30 mL, linear gradient of Buffer A to distilled water was applied, followed by a wash with 0.1% Triton X-100 in. 50 mM sodium phosphate, pH 6.0. One-mL fractions were collected and assayed for both $FB_1$ esterase and for non-specific esterase (as measured by napthyl acetate hydrolysis using the method of Dary et al. (1990) "Microplate adaptation of Gomori's assay for quantitative determination," Journal of Economic Entomology 83:2187–2192. FIG. 2a and b shows the retention times for the specific (i.e. $FB_1$) versus nonspecific (i.e. naphthyl acetate esterase) activities. Both fungal and bacterial $FB_1$ esterase activity eluted at approx. 0.4M ammonium sulfate. Naphthyl acetate esterase activity was detected in both fungal and bacterial cultures but this activity did not co-elute with the $FB_1$ esterase activity. Thus the fungal and bacterial $FB_1$ esterases are not the same as nonspecific esterases detectable in the culture filtrates of these microbes.

EXAMPLE 2

Cloning of Genes Coding for Fumonisin Esterase

Microorganisms demonstrating fumonisin-resistance can be used to create a genomic library using standard techniques, well known in the art. Thus, restriction enzymes can be used to render DNA fragments which can in turn be inserted into any number of suitable cloning vectors. Numerous cloning vectors are known to those of skill in the art, and the selection of an appropriate cloning vector is a matter of choice. The cloning vector need only be capable of transforming a host cell incapable of fumonisin degradation. Examples of recombinant DNA vectors for cloning and host cells which they can transform, shown in parentheses, include the bacteriophage lambda (*E. coli*), pBR322 (*E. coli*), pACYC 177 (*E. coli*, pKT230 (gram-negative bacteria), pGV1106 (gram-negative bacteria), pLAFRI (gram-negative bacteria), pME290 (non-*E. coli* gram-negative bacteria), pIJ61 (Streptomyces), pUC6 (Streptomyces), YIp5 (Saccharomyces), and YCp19 (Saccharomyces). See, generally DNA Cloning, Vols. I and II, supra. and Maniatis et al., supra. Particularly useful is a cloning vector able to transform *E. coli.*

Once the cloning vector has been inserted into an appropriate host cell, the cells are grown on fumonisin containing media and screened for their ability to degrade fumonisin as previously described. Plasmid DNA inserts from colonies that degrade fumonisin are characterized by subcloning, transposon tagging, and DNA sequence analysis, all well within the skill in the art (see, e.g., Napoli, C., and Staskawicz, B. (1987) J. Bact. 169:572–578). Once a coding sequence is determined, recombinant protein molecules able to degrade fumonisin can be produced according to the present invention by constructing an expression cassette and transforming a host cell therewith to provide a cell line or culture capable of expressing the desired protein which is encoded within the expression cassette.

Sequences encoding the fumonisin degradation enzyme can be either prepared directly by synthetic methods based on the determined sequence, or by using the sequence to design oligonucleotide probes to clone the native coding sequence using known techniques. The oligonucleotide probes can be prepared and used to screen a DNA library from an organism able to degrade fumonisin as determined above. The basic strategies for preparing oligonucleotide probes and DNA libraries, as well as their screening by nucleic acid hybridization, are well known to those of ordinary skill in the art. See, e.g., DNA Cloning, Vol. I, supra; Nucleic Acid Hybridization, supra; Oligonucleotide Synthesis, supra; Maniatis et al., supra.

The coding sequence can be comprised entirely of the coding sequence so derived, or such sequences can be fused to other sequences (e.g., leader sequences) so that a fusion protein is encoded. See, e.g. U.S. Pat. Nos. 4,431,739; 4,425,437 and 4,338,397, the disclosures of which are hereby incorporated by reference. Once an appropriate coding sequence for the fumonisin-degrading enzyme has been prepared or isolated, it can be cloned into any suitable vector or replicon, known in the art. These vectors are described above, with *E. coli* being the host bacterium particularly preferred.

To complete construction of the expression cassettes, the coding sequence is then operably linked to control sequences such as a promoter, ribosome binding site (for bacterial expression) and, optionally, an operator, so that the DNA sequence encoding the protein is transcribed into messenger RNA in the host cell transformed by the vector containing the expression construction. It is within the skill of the art to operably link the fumonisin-degrading enzyme coding sequence to appropriate control sequences in order to bring about transcription and translation. In general, the coding sequence will be downstream from the promoter sequence and any expression regulatory regions, such as enhancers or operator sequences. If the coding sequence is linked to a heterologous coding sequence or start codon, then it is important to place the coding sequence in reading frame with the latter. If the intended expression host is procaryotic, then it will also be necessary to include a ribosome binding site among the upstream control sequences. Downstream operably linked control sequences will usually comprise a transcription termination sequence.

The construct can then be inserted into an appropriate expression vector. A number of procaryotic and eucaryotic expression vectors are known in the art. Preferred vectors are procaryotic expression vectors. A particularly preferred host for such vectors is *E. coli.* The fumonisin-degrading enzyme is then produced by growing the host cells transformed by the expression cassette under conditions which cause the expression of the biologically active protein, as indicated by the host cells ability to degrade fumonisin in the medium on which it is grown, as described above. The protein can be isolated from the host cells and purified for further study. If the protein is not secreted, it may be necessary to disrupt the host cells and purify the protein from the cellular lysate. Various purification techniques, such as HPLC, size-exclusion chromatography, electrophoresis, and immunoaffinity chromatography, are known, and the selection of the appropriate purification and recovery method is within the skill of the art.

Similarly, the gene can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey, P. N., and Chua, N. H. (1989) Science 244:174–181. Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion, or via a binary system where the vir gene is present on a separate vector. Such systems, vectors for use therein, and methods of transforming plant cells are described in U.S. Pat. No. 4,658,082; U.S. application Ser. No. 913,914, filed Oct. 1, 1986, as referenced in U.S. Pat. No. 5,262,306, issued Nov. 16, 1993 to Robeson, et al.; and Simpson, R. B., et al. (1986) Plant Mol. Biol. 6:403–415 (also referenced in the '306 patent); all incorporated by reference in their entirety.

Once constructed, these plasmids can be placed into *A. rhizogenes* or *A. tumefaciens* and these vectors used to transform cells of plant species which are ordinarily susceptible to Fusarium infection. For example, non-resistant varieties of tomato (*Lycopersicon esculentum*) are often plagued with such infection and new resistant varieties could be developed to withstand Fusarium-induced wilting in emerging tomato seedlings. Several other transgenic plants are also contemplated by the present invention including but not limited to soybean, corn, sorghum, alfalfa, rice, clover, cabbage, banana, coffee, celery, tobacco, cowpea, cotton, melon and pepper. The selection of either *A. tumefaciens* or *A. rhizogenes* will depend on the plant being transformed thereby. In general *A. tumefaciens* is the preferred organism for transformation. Most dicotyledons, some gymnosperms, and a few monocotyledons (e.g. certain members of the Liliales and Arales) are susceptible to infection with *A. tumefaciens. A. rhizogenes* also has a wide host range, embracing most dicots and some gymnosperms, which includes members of the Leguminosae, Compositae and Chenopodiaceae. Alternative techniques which have proven to be effective in genetically transforming plants include particle bombardment and electroporation. See e.g. Rhodes, C. A., et al. (1988) Science 240, 204–207; Shigekawa, K. and Dower, W. J. (1988) BioTechniques 6,742–751; Sanford, J. C., et al. (1987) Particulate Science & Technology 5:27–37; and McCabe, D. E. (1988) BioTechnology 6:923–926.

Once transformed, these cells can be used to regenerate transgenic plants, capable of degrading fumonisin. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors and cultured under conditions which promote plant regeneration. Roots or shoots transformed by inoculation of plant tissue with *A. rhizogenes* or *A. tumefaciens*, containing the gene coding for the fumonisin degradation enzyme, can be used as a source of plant tissue to regenerate fumonisin-resistant transgenic plants, either via somatic embryogenesis or organogenesis. Examples of such methods for regenerating plant tissue are disclosed in Shahin, E. A. (1985) Theor. Appl. Genet. 69:235–240; U.S. Pat. No. 4,658,082; Simpson, R. B., et al. (1986) Plant Mol. Biol. 6:403–415; and U.S. patent applications Ser. Nos. 913,913 and 913,914, both filed Oct. 1, 1986, as referenced in U.S. Pat. No. 5,262,306, issued Nov. 16, 1993 to Robeson, et al.; the entire disclosures therein incorporated herein by reference.

Certain esterases fall into a family that is related by primary sequence and overall structure (Cygler M, Schrag J D, Sussman J L, Harel M, Silman I, Gentry M K, Doctor BP (1993) "Relationship between sequence conservation and 3-Dimensional structure in a large family of esterases, lipases, and related proteins." Protein Sci 2:366–382.). PCR primers were designed based on highly conserved regions of this esterase family and using these primers, a cDNA clone from *Exophiala spinifera* isolate 2141.10 was obtained that showed significant homology to known esterases, and was specifically induced by fumonisin and other inducers. This esterase can be expressed in *E. coli* and its enzyme activity can be measured by means of the TLC assay described above. If no activity is obtained in *E. coli* then expression can be measured in yeast or another eukaryotic system.

Other methods can also be used to clone the gene. Purification of the protein and N-terminal sequencing allow design of specific DNA probes; generation of antibodies from purified protein and screening an expression library; using RNA enrichment methods to obtain cDNAs specific to the induced culture. Once the gene has been confirmed as corresponding to fumonisin esterase, the cDNA clone can easily be ligated into appropriate expression vectors for expression of the enzyme in maize tissue culture cells, transgenic maize, and also in *Fusarium moniliforme* itself, that is useful for studying the mechanisms of pathogenesis associated with the fungus and its toxin. Transformed or transient-expressing maize tissue culture cells can then be evaluated for resistance to fumonisins relative to control transformed tissue, and in fact fumonisin can be used as a selection agent to isolate transformed cells from tissue culture.

EXAMPLE 3

Preparation of AP1-induced and Non-Induced Mycelium

*Exophiala spinifera* isolate 2141.10 was grown in YPD broth for 5 days at 28° C., mycelium was harvested on 05. micron cellulose acetate filters and transferred to fresh medium consisting of Fries mineral salts (Gilchrist D G, Grogan R G (1976) "Production and nature of a host-specific toxin from *Alternaria alternata* f. sp. lycopersici." Phytopathology 66:165–171) amended with hydrolyzed fumonisin B1 (AP1) (0.5 mg/mL) or delta-aminobutyric acid (δ-ABA) (1 mg/mL) as the sole carbon source. Cultures were incubated in the dark for 48 hr at 28° C. and culture supernalants removed by filtration through 0.5 micron cellulose acetate. The remaining mycelial mat was washed with sterile Fries mineral salts and then frozen in liquid nitrogen for storage.

EXAMPLE 4

RNA Isolation from *Exophiala spinifera*

The mycelial mats described above (~1 gram) were ground in liquid nitrogen in a mortar and pestle following addition of 10 mL "TRIREAGENT" (Molecular Research Center, Inc. Cincinnati, Ohio) in the presence of 0.2 volume chloroform. The grindate was centrifuged and the resulting supernatant precipitated with isopropanol. The resulting pellet was extracted with phenol, ethanol precipitated, and stored at −80° C.

The RNA in water (0.4 mL) was enriched for poly-A-containing mRNA using biotin-oligo(dT) and a streptavidin magnetic bead system (Promega) using the manufacturer's instructions. The polyA(+)-enriched RNA was stored at −80° C.

First strand cDNA synthesis from polyA(+)-enriched RNA was carried out using M-MLV reverse transcriptase (37° C., 1 hr). The reaction mixture was extracted with phenol and chloroform. Aliquots were taken for polymerase chain reaction (PCR) using the degenerate primers identified in SEQUENCE I.D. NOS. 1 through 4.:

ESP5'-OL1 GGGGAATTCGARGAYTGNYTNTAYNT-NAAYRT (SEQUENCE I.D. NO. 1)

ESP5'-OL2 GGGGAATTCMCNGTNNTNVTNTGGAT-NYAYGGNGGNG (SEQUENCE I.D. NO. 2)

ESP3'-OL1 GGGAAGCTTGGRTYNCCNCCRAANK-BNGCDATRTY (SEQUENCE I.D. NO. 3)

ESP3'-OL2 GGGAAGCTTCNCCNGCNSWYTCNC-CRAANADNGTNA (SEQUENCE I.D. NO. 4)

Most bases designated "N" were inosines.

Thermocycler reaction conditions were:

1. 94° C. 2 min
2. 94° C. 30 sec
3. 45° C. 2 min
4. 72° C. 1 min
5. repeat steps 2–4 for 35 X
6. 72° C. 5 min The PCR reaction products were electrophoresed on horizontal agarose gels. Bands that were present only in induced lanes were excised and the DNA was eluted. The recovered DNA was digested with HindIII and EcoRI and ligated into pBluescript SK+. A recombinant clone from products amplified using ESP5'-OL2 and ESP3'-OL2 (ESP26-1) was recovered and sequenced. The cloned region contains an open reading frame with the partial protein or amino acid sequence ... SFHLYDGASFAANQDVIVVTINYRT-NILGFPAAPQLPITQRNLGFLDQRFALDWV QRNIAAFGGDPRKVT FFGESA ... (SEQUENCE I.D. NO. 5)

The above deduced amino acid sequence from DNA fragment ESP26-1 showed significant homology to a family of proteins that includes cholinesterases, acetylcholinesterases, carboxylesterases, and certain lipases (Cygler M, Schrag J D, Sussman J L, Harel M, Silman I, Gentry M K, Doctor B P (1993)"Relationship between sequence conservation and 3-Dimensional structure in a large family of esterases, lipases, and related proteins." Protein Sci 2:366–382.)

EXAMPLES 5–6

Comparison of Deduced Amino Acid Sequence to Known Sequences

In comparison with a sequence published in Arpagaus, M., Chatonnet, A., Masson, P., Newton, M., Vaughan, T. A., Bartels, C. F., Nogueira, C. P., La Du, B. N., and Lockridge, O. J. Biol. Chem. 266, 6966–6974 (1991), 43 of the 76 amino acids in ESP26-1 were identical to a dog pancreatic cholinesterase.

In another comparison 32 of 62 amino acids from ESP26-1 were identical to a fungal lipase, as published by Lotti, M., Grandori, R., Fusetti, F., Longhi, S., Brocca, S., Tramontano, A., and Alberghina, L., Gene 124, 45–55 (1993).

EXAMPLE 7

Northern Blot Analysis of Induced, Non-Induced *Exophiala Spinifera*

Total RNA extracted from *Exophiala spinifera* cultures as described in the preceding examples was electrophoresed on agarose gels containing formaldeyde, blotted to nitrocellulose, and probed with random-primed 32P-labelled ESP26-1 cDNA. The probe hybridized to an RNA of approximately 2.0 kilobases in size in the induced lane, but not in the non-induced lane (see FIG. 1).

EXAMPLE 8

Isolation of Full Length cDNA of ESP26-1 from *Exophiala spinifera*

To obtain 3'-end of the cDNA coding for the putative esterase, a 3'-rapid amplification of cDNA ends protocol (3'-RACE) was employed (Frohman, M. A., Dush, M. K., and Martin, G. R. 1988 "Rapid production of full-length cDNAs from rare transcripts: Amplification using a single gene-specific oligonucleotide primer." Proc. Natl. Acad. Sci. 85: 8998–9002). 5 µg of total RNA isolated from AP1 induced *Exophiala spinifera*. mycelia was used as template for reverse transcription reaction. The reverse transcription reaction and subsequent PCR amplification was performed with a 3'-RACE kit (Gibco BRL). The gene-specific primer (ESP3'- 1:

GCTAGTTTCGCAGCCAATCA-GGA) (SEQUENCE I.D. NO. 6) was designed based on ESP26-1 sequence.

PCR reaction conditions were:

1. 94° C. 4 min
2. 94° C. 45 sec
3. 60° C. 25 sec
4. 72° C. 3 min
5. repeat steps 2–4 for 40 X
6. 72° C. 10 min A resulting 1.5 kb DNA fragment was blotted to nitrocellulose and hybridized with cDNA ESP26-1 under highly stringent hybridization and wash conditions (last wash: 0.1×SSC, 0.5% SDS, 65° C. for 30 min.) The DNA fragment was gel-isolated, ligated into a pGEM-T vector (Promega), and transformed into DH5_(Gibco BRL). The resulting plasmid DNA (p3RC-2) was sequenced using M 13 universal primer. Sequence comparison of 3RC-2 and ESP26-1 indicated the ESP26-1 overlapped 100% with the 5' end of 3RC-2 sequence.

To obtain the amino-terminal sequence, a 5'-RACE strategy was employed (Frohman, et al., supra). 5 µg of total RNA isolated from AP1 induced *Exophiala spinifera*. mycelia was reverse transcribed with SuperScript I RNase H-reverse Transcriptase (Gibco BRL) using an anti-sense primer constructed ESP26-1 sequence (ESP5'-1: AAAGGCTGCGATGTTCCGCTGTA) (SEQUENCE I.D. NO. 7). The cDNA was tailed with dATP using terminal transferase (Promega) and used as a template for nested amplification using a second gene-specific anti-sense primer (ESP5'-2: TCGCTGTGTTATTGGCAGCTGAG. (SEQUENCE I.D. NO. 8). C was a silent mutation of A in order to create a Pvu II restriction site) and an end-blocked polyT primer (BamT17V: CGCGGATCCGTTTTTTTTTTTTTTTTV) (SEQUENCE I.D. NO. 9).

PCR reaction conditions were:

1. 94° C. 4 min
2. 94° C. 45 sec
3. 40° C. 45 sec
4. 60° C. 25 sec
5. 72° C. 3 min
6. repeat steps 2–5 for 41 X
7. 72° C. 10 min The PCR products were fractionated on a 1.5% agarose gel. The amplified product was gel-isolated, ligated into pGEM-T (Promega), and transformed into DH5 (Gibco BRL). The resulting 5' RACE product was sequenced and shown to overlap as expected with the 3' RACE product and to contain an open reading frame with significant homology to members of the serine esterase/lipase superfamily described by Cygler et al. (supra). The overlapping sequences obtained by 3' RACE and 5' RACE were combined to yield a cDNA sequence corresponding to the complete open reading frame. The full length, 1937 bp cDNA clone from *Exophiala spinifera* 2141.10 (abbreviated ESP1) contains an open reading frame of 537 amino acids as shown below (SEQUENCE I.D. NO. 10).

MPSRYILSWLLTCFLGIAFG-
SRCGSSAPTVKIDAGMVVGTTTTVPGTTATVSEFLG
V PFAAS PTRFAPPTRPVPWSTPLQATAYG-
PACPQQFNYPEELREITMAWFNTPPPS A GESED-
CLNLNIYVPGTENTNKAVMVWIYGGA-
LEYGWNSFHLYDGASFAANQDVI
VVTINYRTNILGFPAAPQLPITQRNLG-
FLDQRFALDWVQRNIAAFGGDPRKVTIFG QSAG-
GRSVDVLLTSMPHNPPFRAAIMESG-
VANYNFPKGDLSEPWNTTVQALNCT
TSIDILSCMRRVDLATLMNTIEQLGLG-
FEYTLDNVTVVYRSETARTrGDIARVPVL VGT-
VANDGLLFVLGENDTQAYLEEAIPNQPD-
LYQTLLGAYPIGSPGIGSPQDQIAAI
ETEVRFQCPSAIVAQDSRNR-
GIPSWRYYYNATFENLELFPGSEVYHSSEVGMVFGT
YPVASATALEAQTSKYMQGAWAAFAKNP-
MNGPGWKQVPNVAALGSPGKAIQVD VSPATIDQR-
CALYTHYYTELGTIAPRTF

This open reading frame (ORF) shows some homology to members of the serine esterase/lipase superfamily described by Cygler et al. (supra). The most extensive homology is 35.9% identity in 320 amino acid overlap with butyrylcholinesterase from *Oryctolagus cuniculus* (rabbit).

The deduced Esp1 protein contains a putative signal peptide which is probably cleaved at position 26/27 yielding a mature protein with a calculated MW of 54953.781 and calculated pI of 4.5. These calculated values are consistent with the estimated MR and pI of the fumonisin esterase activity described above.

A comparison of the Esp1 open reading frame consensus regions in the esterase superfamily (Cygler et al., supra) reveals numerous conserved features indicating Esp1 may code for a serine esterase. The Esp protein has a potential serine active site consensus at 223–228; a putative aspartate active site consensus at 335–341 that is typical of cholesterol esterases and Drosophohila 6 and P proteins [the majority of members of this superfamily, including fungal lipases and carboxylesterases have E at the active site instead of D]; and a putative histidine active site that is different from any members of the family, containing additional amino acids between the G and H. The putative Esp mature protein has a total of 6 cysteines, for 3 possible disulfide bridges, consistent with at least a subset of the esterases in the superfamily described by Cygler et al., supra Thus the Esp ORF has most of the hallmarks of a bona fide member of the lipase/esterase superfamily, including a putative active site triad and other conserved amino acids. The regions of conservation are not consistent with any one substrate subgroup (i.e. lipase, cholinesterase, carboxlylesterase, or cholesterol esterase), but seem to be contain some features of several of these, and Esp appears to be unique among known esterases in its putative active site His consensus sequence.

EXAMPLE 9

Effect of $FB_1$ and AP1 on Maize Coleoptiles

Maize coleoptiles from 4 day dark-grown germinated maize seeds were excised above the growing point and placed in 96-well microtiter plates in the presence of 60 microliters of sterile distilled water containing $FB_1$ or $AP_1$ at approximately equimolar concentrations of 1.5, 0.5, 0.15, 0.05, 0.015, 0.005, 0.0015, or 0.0005 millimolar, along with water controls. After 2 days in the dark at 28° C. the coleoptiles were placed in the light and incubated another 3 days. Injury or lack thereof was evaluated as follows:

| | 0 | .0005 | .0015 | .005 | .015 | .05 | .15 | .5 | 1.5 | mM |
|---|---|---|---|---|---|---|---|---|---|---|
| $FB_1$ | − | − | − | − | +/− | + | + | + | + | |
| AP1 | − | − | − | − | − | − | − | − | + | |

+ = brown necrotic discoloration of coleoptile
− = no symptoms (same as water control)

The results (see table above) indicate there is at least a 30-fold difference in toxicity between $FB_1$ and $AP_1$ to maize coleoptiles of this genotype. This is in general agreement with other studies where the toxicity of the two compounds was compared for plant tissues: In Lemna tissues, $AP_1$ was approx. 40-fold less toxic (Vesonder RF, Peterson R E, Labeda D, Abbas H K (1992) "Comparative phytotoxicity of the fumonisins, AAL-Toxin and yeast sphingolipids in *Lemna minor* L (Duckweed)." Arch Environ Contam Toxicol 23:464–467.). Studies with both AAL toxin and $FB_1$ in tomato also indicate the hydrolyzed version of the molecule is much less toxic (Gilchrist D G, Ward B, Moussato V, Mirocha C J (1992) "Genetic and Physiological Response to Fumonisin and AAL-Toxin by Intact Tissue of a Higher Plant." Mycopathologia 117:57–64.). In a recent report Lamprecht et al. also observed an approximate 100-fold reduction in toxicity to tomato by $AP_1$ versus $FB_1$ (Lamprecht S, Marasas W, Alberts J, Cawood M, Gelderblom W, Shephard G, Thiel P, Calitz J (1994) Phytotoxicity of fumonisins and TA-toxin to corn and tomato. Phytopathology 84:383391.)

EXAMPLE 10

Effect of $FB_1$ and $AP_1$ on Maize Tissue Cultured Cells (Black Mexican Sweet, BMS)

$FB_1$ or $AP_1$ at various concentrations was added to suspensions of BMS cells growing in liquid culture medium in 96-well polystyrene plates. After 1 week the cell density in wells was observed under low power magnification and growth of toxin-treated wells was compared to control wells that received water. Growth of BMS cells was significantly inhibited at 0.4 micromolar $FB_1$, but no inhibition was observed until 40 micromolar $AP_1$. This represents an approximate 100-fold difference in toxicity to maize tissue cultured cells. Similarly Van Asch et al. (Vanasch M A J, Rijkenberg F H J, Coutinho T A (1992) "Phytotoxicity of fumonisin b1, moniliformin, and t-2 toxin to corn callus cultures." Phytopathology 82:1330–1332) observed significant inhibition of maize callus grown on solid medium at 1.4 micromolar. $AP_1$ was not tested in that study, however.

What is claimed is:

1. An isolated enzyme having the structure of the fumonisin degradative enzyme produced by *Exophiala spinifera*, ATCC 74269, *Rhinocladiella atrovirens*, ATCC 74270, or the bacterium of ATCC 55552 in the presence of a fumonisin.

2. An isolated $AP_1$ catabolase, capable of detoxifying a fumonisin hydrolysis product, which is produced by fermentation of one or more of *Exophiala spinifera*, ATCC 74269, *Rhinocladiella atrovirens*, ATCC 74270, or the bacterium of ATCC 55552.

3. An isolateed protein having the sequence of SEQ. ID NO. 10.

* * * * *

UNITED STATES PATENT AND TRADEMARK OFFICE
CERTIFICATE OF CORRECTION

PATENT NO. : 5,716,820
DATED : February 10, 1998
INVENTOR(S) : Jon Duvick, Tracy Rood and Xun Wang It is certified that error appears in the above-identified patent and that said Letters Patent is hereby corrected as shown below:

Claim 3, at column 36, line 4, should read as follows:

3. An isolated protein having the sequence of SEQ. ID NO. 10.

Signed and Sealed this

Fifth Day of May, 1998

Attest:

BRUCE LEHMAN

*Attesting Officer*    *Commissioner of Patents and Trademarks*